(12) United States Patent
Iwanami et al.

(10) Patent No.: US 11,181,730 B2
(45) Date of Patent: Nov. 23, 2021

(54) ENDOSCOPE LEAK TEST CONNECTOR, ENDOSCOPE LEAK TESTER AND ENDOSCOPE REPROCESSOR

(71) Applicant: OLYMPUS CORPORATION, Tokyo (JP)

(72) Inventors: Takayoshi Iwanami, Hachioji (JP); Koichiro Okada, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 182 days.

(21) Appl. No.: 16/751,524

(22) Filed: Jan. 24, 2020

(65) Prior Publication Data
US 2020/0159004 A1    May 21, 2020

Related U.S. Application Data

(63) Continuation of application No. PCT/JP2018/017500, filed on May 2, 2018.

(30) Foreign Application Priority Data

Aug. 28, 2017    (JP) .............................. JP2017-163661

(51) Int. Cl.
*G02B 23/24*    (2006.01)
*A61B 1/12*    (2006.01)
(Continued)

(52) U.S. Cl.
CPC ................ *G02B 23/24* (2013.01); *A61B 1/12* (2013.01); *G01M 3/04* (2013.01); *G01M 3/26* (2013.01);
(Continued)

(58) Field of Classification Search
CPC ........... A61B 1/12; G02B 23/24; G01M 3/26; G01M 3/04; G01M 3/3236; G01M 3/3227; G01M 3/2876
(Continued)

(56) References Cited

U.S. PATENT DOCUMENTS 6,582,654 B1 *   6/2003   Kral .................... A61B 1/123
                                                              134/161
10,582,832 B2 *  3/2020   Lawrence ............ A61B 1/0607
(Continued)

FOREIGN PATENT DOCUMENTS

JP    2005-204836 A    8/2005
JP    2013-042790 A    3/2013
(Continued)

OTHER PUBLICATIONS

International Search Report dated Jun. 5, 2018 issued in PCT/JP2018/017500.

*Primary Examiner* — Clayton E. LaBalle
*Assistant Examiner* — Kevin C Butler
(74) *Attorney, Agent, or Firm* — Scully, Scott, Murphy & Presser, P.C.

(57) ABSTRACT

An endoscope leak test connector includes: a rotating body configured to cause a ventilation member to project from a leak test pipe sleeve by rotating in a positive direction and cause the ventilation member to be buried into the leak test pipe sleeve by rotating in a negative direction; a gas inlet configured to be connected with a gas supply source; a facing member configured to face the ventilation member projecting from the leak test pipe sleeve; a gas outlet that is open on the facing member; and a seal portion configured to seal the gas outlet and the ventilation member so that the gas outlet and the ventilation member liquid-tightly communicate with each other.

10 Claims, 12 Drawing Sheets

(51) Int. Cl.
  *G01M 3/32* (2006.01)
  *G01M 3/04* (2006.01)
  *G01M 3/28* (2006.01)
  *G01M 3/26* (2006.01)

(52) U.S. Cl.
  CPC ........ *G01M 3/2876* (2013.01); *G01M 3/3227* (2013.01); *G01M 3/3236* (2013.01)

(58) Field of Classification Search
  USPC .............................................. 73/40; 600/158
  See application file for complete search history.

(56) References Cited

U.S. PATENT DOCUMENTS

| | | | | |
|---|---|---|---|---|
| 2002/0001537 | A1* | 1/2002 | Hlebovy | A61L 2/18 422/28 |
| 2016/0095508 | A1* | 4/2016 | Terliuc | G01M 3/3272 134/18 |
| 2017/0020367 | A1* | 1/2017 | Tomita | A61B 1/00 |
| 2017/0086663 | A1* | 3/2017 | Iwanami | B08B 9/032 |
| 2018/0304315 | A1* | 10/2018 | Connelly | A61B 1/125 |
| 2019/0142244 | A1* | 5/2019 | Lengsfeld | F16K 31/001 600/158 |
| 2020/0159004 | A1* | 5/2020 | Iwanami | A61B 1/00057 |

FOREIGN PATENT DOCUMENTS

| | | |
|---|---|---|
| JP | 2015-070947 A | 4/2015 |
| JP | 2016-182264 A | 10/2016 |
| JP | 2017-070426 A | 4/2017 |
| JP | 2017-113152 A | 6/2017 |

\* cited by examiner

ENDOSCOPE LEAK TEST CONNECTOR, ENDOSCOPE LEAK TESTER AND ENDOSCOPE REPROCESSOR

CROSS REFERENCE TO RELATED APPLICATION

This application is a continuation application of PCT/JP2018/017500 filed on May 2, 2018 and claims benefit of Japanese Application No. 2017-163661 filed in Japan on Aug. 28, 2017, the entire contents of which are incorporated herein by this reference.

BACKGROUND OF THE INVENTION

1. Field of the Invention

The present invention relates to an endoscope leak test connector, an endoscope leak tester and an endoscope reprocessor.

2. Description of the Related Art

Conventionally, a leak test for testing whether an internal space of an endoscope maintains liquid-tightness or air-tightness has been performed before using the endoscope for a subject or object. In the leak test, gas is fed into the internal space of the endoscope, and liquid-tightness or air-tightness judgment is performed according to a leakage state of the fed gas.

For example, Japanese Patent Application Laid-Open Publication No. 2013-42790 discloses an endoscope, wherein an endoscope leak test connector of an air feeding tester is connected with a leak test pipe sleeve provided on the endoscope; compressed air is fed into an internal space of the endoscope from the air feeding tester to inflate a balloon; the endoscope leak test connector is removed from the leak test pipe sleeve; the endoscope is immersed in liquid of a cleaning apparatus and cleaned; and an air-tightness state of the endoscope is tested by observing a state of the balloon.

SUMMARY OF THE INVENTION

An endoscope leak test connector of an aspect of the present invention includes: a cover face including a connection portion-side engagement portion configured to be non-liquid-tightly engaged with a pipe-sleeve-side engagement portion of a leak test pipe sleeve for an endoscope, the leak test pipe sleeve including a rotating ring, the pipe-sleeve-side engagement portion being provided on the rotating ring, and a ventilation member configured to project and be buried in conjunction with a rotation operation of the rotating ring, the cover face non-liquid-tightly covering an outer circumferential portion of the leak test pipe sleeve; a rotating body including the cover face on an inner side and configured to cause the ventilation member to project from the leak test pipe sleeve by rotating in a positive direction and cause the ventilation member to be buried into the leak test pipe sleeve by rotating in a negative direction; a gas inlet configured to be connected with a gas supply source; a facing member configured to face the ventilation member that is in a state of projecting from the leak test pipe sleeve; a gas outlet communicating with the gas inlet and being open on the facing member; and a seal portion arranged on the facing member and configured to seal the gas outlet and the ventilation member so that the gas outlet and the ventilation member liquid-tightly communicate with each other.

An endoscope leak test connector of another aspect of the present invention includes: a cover face including a connection portion-side engagement portion configured to be non-liquid-tightly engaged with a pipe-sleeve-side engagement portion of a leak test pipe sleeve for an endoscope, the leak test pipe sleeve including the pipe-sleeve-side engagement portion and a ventilation member capable of projecting and being buried, the cover face non-liquid-tightly covering an outer circumferential portion of the leak test pipe sleeve; an operating member including the cover face on an inner side and configured to cause the ventilation member to be buried into the leak test pipe sleeve by causing the ventilation member to project from the leak test pipe sleeve; a gas inlet configured to be connected with a gas supply source; a facing member configured to face the ventilation member that is in a state of projecting from the leak test pipe sleeve; a gas outlet communicating with the gas inlet and being open on the facing member; and a seal portion arranged on the facing member and configured to seal the gas outlet and the ventilation member so that the gas outlet and the ventilation member liquid-tightly communicate with each other.

An endoscope leak tester of an aspect of the present invention includes: the endoscope leak test connector; and a gas supply source configured to be connected with the gas inlet.

Furthermore, an endoscope reprocessor of an aspect of the present invention includes: the endoscope leak test connector; a treatment tank configured so that the endoscope is arranged; a gas supply source; and a reprocessor connection portion arranged in the treatment tank, communicating with the gas supply source and configured to be connected with the gas inlet.

DETAILED DESCRIPTION OF THE PREFERRED EMBODIMENTS

Embodiments of the present invention will be described below with reference to drawings.

First Embodiment

Figure 1:
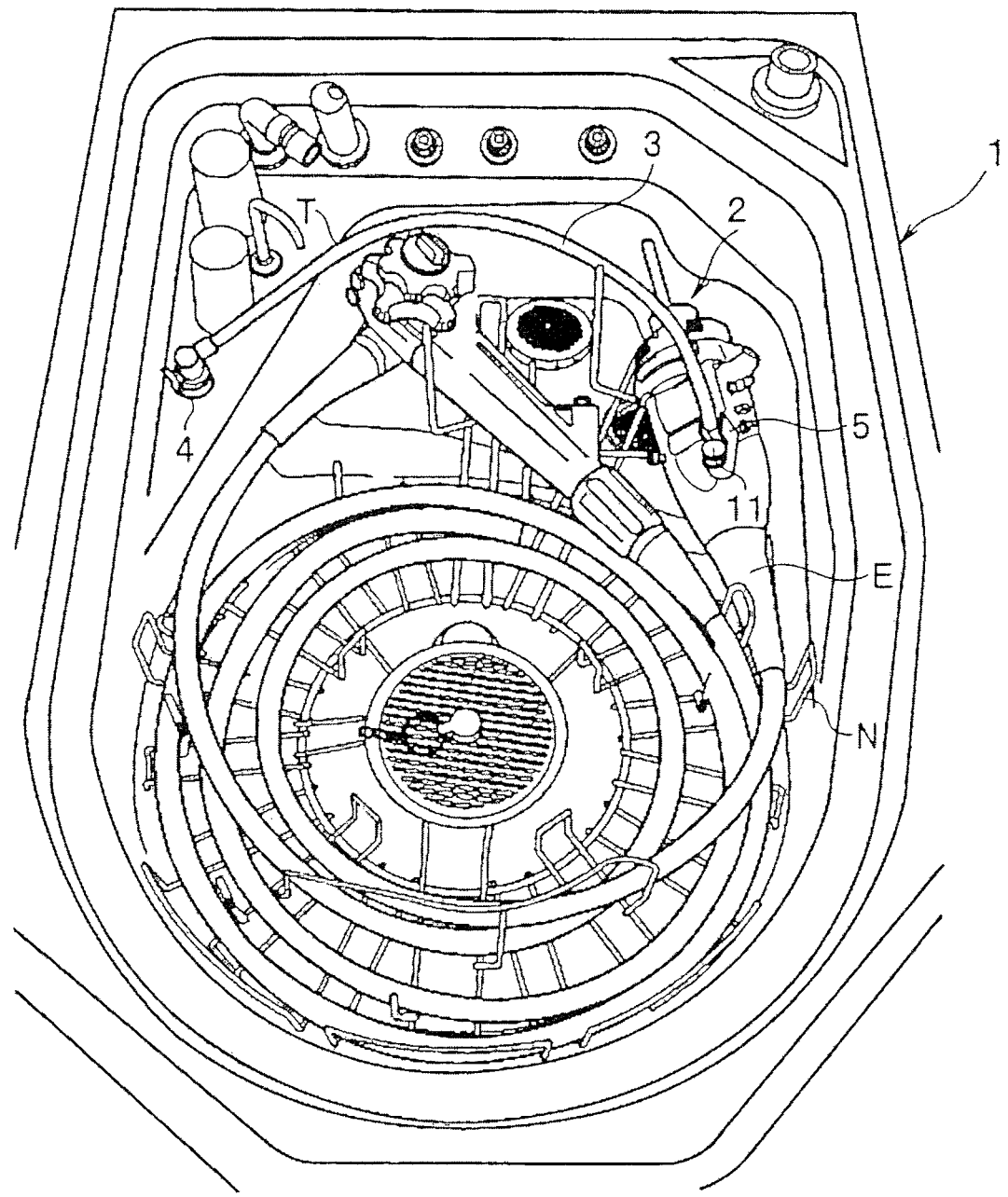
FIG. 1 is an explanatory diagram for illustrating an example of a treatment tank of an endoscope reprocessor according to a first embodiment of the present invention.

FIG. 1 is an explanatory diagram for illustrating an example of a treatment tank 2 of an endoscope reprocessor 1 according to a first embodiment.

The endoscope reprocessor 1 is an apparatus to perform reprocessing of a contaminated endoscope E, and parts, attachments or the like of the endoscope E. The reprocessing stated here is not especially limited and may be any of rinsing with water, cleaning to remove dirt such as organic substances, disinfection to deactivate predetermined microorganisms, sterilization to cause all microorganisms to be eliminated or die out, or a combination of these processes. The attachments are not especially limited, and examples of the attachments include a suction button, an air/water feeding button, and a distal end cover configured to cover a distal end portion of the endoscope E which are fitted to the endoscope E at the time of being used and is removed from the endoscope E at the time of being reprocessed.

As shown in FIG. 1, the endoscope reprocessor 1 has the treatment tank 2. The endoscope E is accommodated in the treatment tank 2 in a state of being held by a holding net N.

The endoscope E and the endoscope reprocessor 1 are connected via an endoscope leak test connector 3. The endoscope leak test connector 3 has a tube T, an endoscope reprocessor connection portion 4 provided on one end portion and an endoscope connection portion 5 provided on the other end portion.

(Configuration of Leak Test Pipe Sleeve 11)

First, a leak test pipe sleeve 11 of the endoscope E configured to be connected to the endoscope connection portion 5 will be described.

Figure 2:
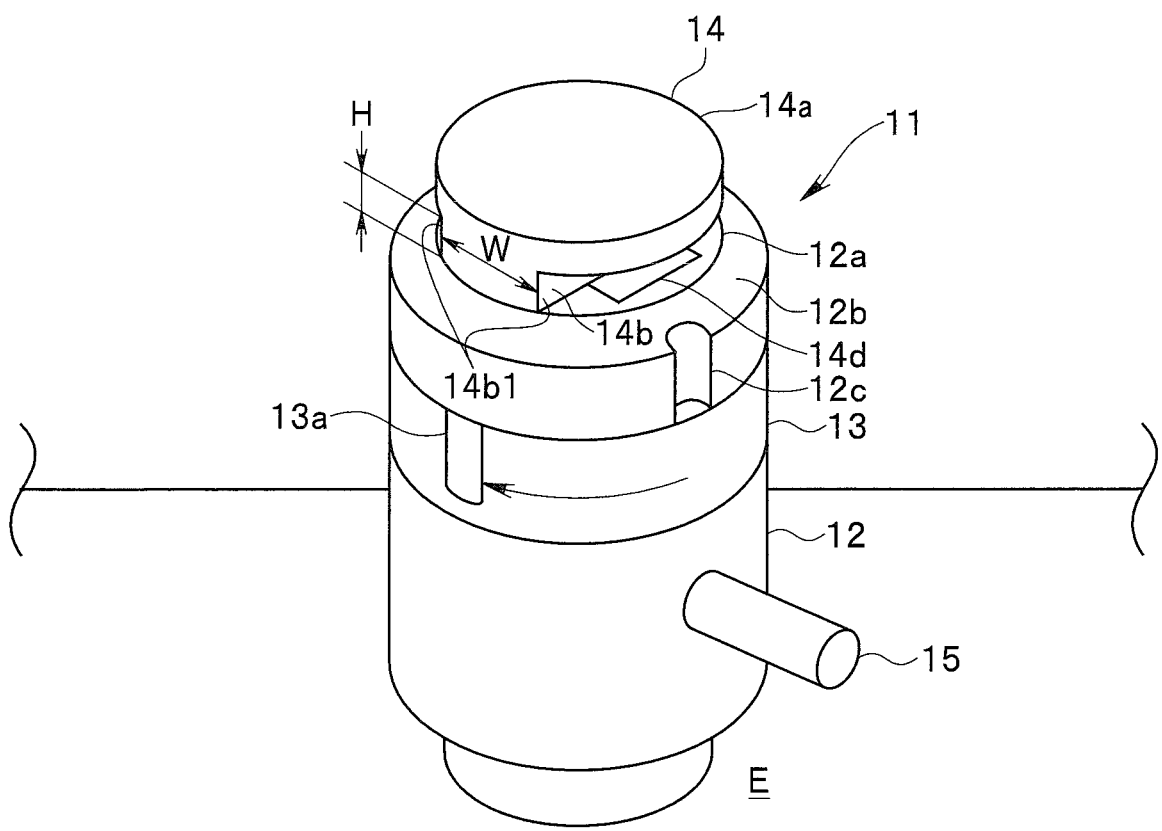
FIG. 2 is a perspective view showing an example of a leak test pipe sleeve configured to be connected to an endoscope connection portion of an endoscope leak test connector according to the first embodiment of the present invention.
Figure 3:
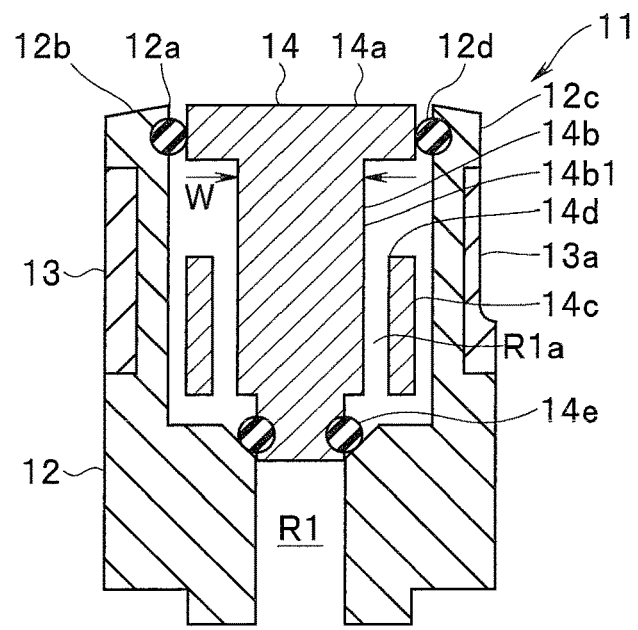
FIG. 3 is a cross-sectional view showing the example of the leak test pipe sleeve configured to be connected to the endoscope connection portion of the endoscope leak test connector according to the first embodiment of the present invention.
Figure 4:
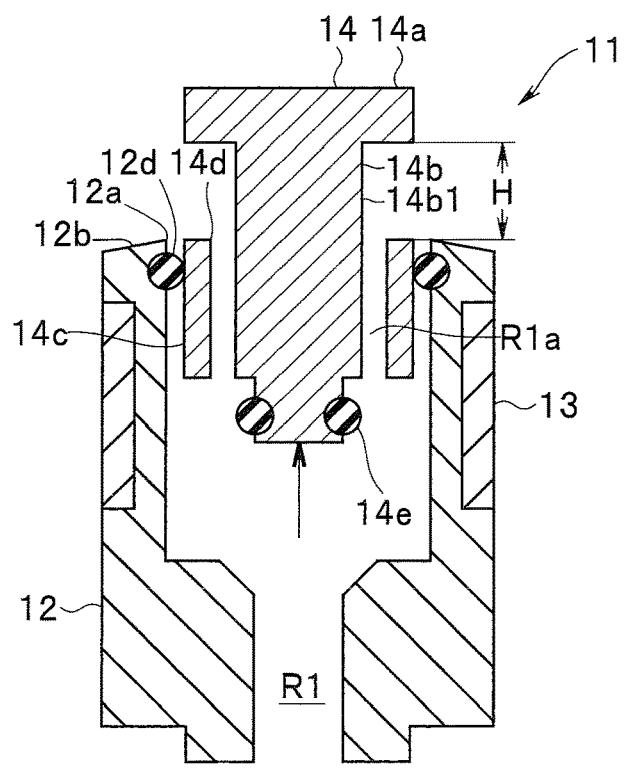
FIG. 4 is a cross-sectional view showing the example of the leak test pipe sleeve configured to be connected to the endoscope connection portion of the endoscope leak test connector according to the first embodiment of the present invention.

FIGS. 2 to 4 are diagrams showing an example of the leak test pipe sleeve 11 configured to be connected to the endoscope connection portion 5 of the endoscope leak test connector 3 according to the first embodiment of the present invention. FIG. 2 is a perspective view, and FIGS. 3 and 4 are cross-sectional views. FIGS. 3 and 4 show sections of the endoscope connection portion 5.

As shown in FIG. 2, the leak test pipe sleeve 11 is provided on the endoscope E and is configured to be capable of being connected with the endoscope connection portion 5. The leak test pipe sleeve 11 has a trunk portion 12, a rotating ring 13, a ventilation member 14 and a projecting portion 15.

The trunk portion 12 is projectingly provided on the endoscope E. The trunk portion 12 is formed in a tubular shape, for example, using metal as material. The trunk portion 12 has a flow path R1 inside. The trunk portion 12 has a distal end opening 12a, a distal end circumferential edge 12b and a through recess portion 12c, and an O-shaped ring 12d is attached to the trunk portion 12.

The distal end opening 12a is provided in a central part of a distal end face of the trunk portion 12.

The distal end circumferential edge 12b is provided on a circumferential edge of the distal end opening 12a and is formed inclining in a proximal end direction from an inner edge to an outer edge in a chamfered state.

The through recess portion 12c is provided on an outer circumferential portion of the trunk portion 12 on a distal end side and is formed in a through recess shape passing through from the distal end circumferential edge 12b to a distal end of the rotating ring 13 so that a connection-portion-side engagement portion 25 can move from the distal end circumferential edge 12b side to a pipe-sleeve-side engagement portion 13a.

The O-shaped ring 12d is configured using rubber or the like as material and is attached to an inner circumferential portion of the trunk portion 12 on the distal end side.

The rotating ring 13 is configured, for example, of metal. The rotating ring 13 is provided on the outer circumferential portion of the trunk portion 12 in a circumferential direction and is formed in a ring shape. The rotating ring 13 is rotatable in the circumferential direction. The rotating ring 13 has the pipe-sleeve-side engagement portion 13a formed in a recess shape so that rotation force is transmitted from the endoscope connection portion 5. The rotating ring 13 transmits rotation force received from the endoscope connection portion 5 to the ventilation member 14 by a power transmission mechanism not shown.

The ventilation member 14 is configured, for example, of metal. The ventilation member 14 is projectably and retractably provided along the inner circumferential portion of the trunk portion 12, and ventilation is enabled by the ventilation member 14 projecting from the trunk portion 12. The ventilation member 14 is formed, for example, in a cylindrical shape and has a power transmission mechanism such as a feed screw not shown. The ventilation member 14 has a lid portion 14a, a neck portion 14b, a ventilation member body 14c, a ventilation member opening 14d and an O-shaped ring 14e.

The lid portion 14a is provided on the distal end side of the ventilation member 14 and is formed in a disk shape.

The neck portion 14b is provided being extended in a proximal end direction from the lid portion 14a and is formed in a manner of cutting out a part of an outer circumference. For example, the neck portion 14b has a pair of parallel side faces 14b1 formed by cutting out both sides of an outer circumferential portion by two planes extending in an insertion direction Di and intersecting a circumferential wall, the parallel side faces 14b1 being formed in a manner of facing each other in parallel. A width of the neck portion 14b in a transverse direction is set to a predetermined width W.

As shown in FIGS. 3 and 4, the ventilation member body 14c is provided being extended in a proximal end direction from the neck portion 14b. The ventilation member body 14c has a flow path R1a inside, the flow path R1a communicating with the flow path R1.

The ventilation member opening 14d is provided to be next to the neck portion 14b and communicates with the flow path R1a. In other words, the ventilation member opening 14d is provided inside the leak test pipe sleeve 11.

The O-shaped ring 14e is configured using rubber or the like as material and is attached to an outer circumferential portion of the ventilation member body 14c on a proximal end side.

The projecting portion 15 is projectingly provided outward from a proximal end portion of the trunk portion 12 (FIG. 2).

When the rotating ring 13 rotates in a negative direction by a predetermined angle, the ventilation member 14 is buried into the trunk portion 12 as shown in FIG. 3. An outer circumferential portion of the lid portion 14a presses against the O-shaped ring 12d; the O-shaped ring 14e presses against the inner circumferential portion of the trunk portion 12 on the proximal end side; and the leak test pipe sleeve 11 enters a valve closed state.

When the rotating ring 13 rotates in a positive direction by a predetermined angle, the ventilation member 14 projects from the trunk portion 12 so that the neck portion 14b is exposed by a predetermined height H as shown in FIG. 4. The ventilation member opening 14d is exposed outside; the O-shaped ring 12d moves away from the lid portion 14a and presses against the outer circumferential portion of the ventilation member body 14c; the O-shaped ring 14e moves away from the inner circumferential portion of the trunk portion 12 on the proximal end side; and the leak test pipe sleeve 11 enters a valve opened state.

In other words, the leak test pipe sleeve 11 is provided with the rotating ring 13, the pipe-sleeve-side engagement portion 13a provided on the rotating ring 13 and the ventilation member 14 which projects or is buried in conjunction with a rotation operation of the rotating ring 13.

(Configuration of Endoscope Connection Portion 5)

Next, a configuration of the endoscope connection portion 5 of the endoscope leak test connector 3 will be described.

Figure 5:
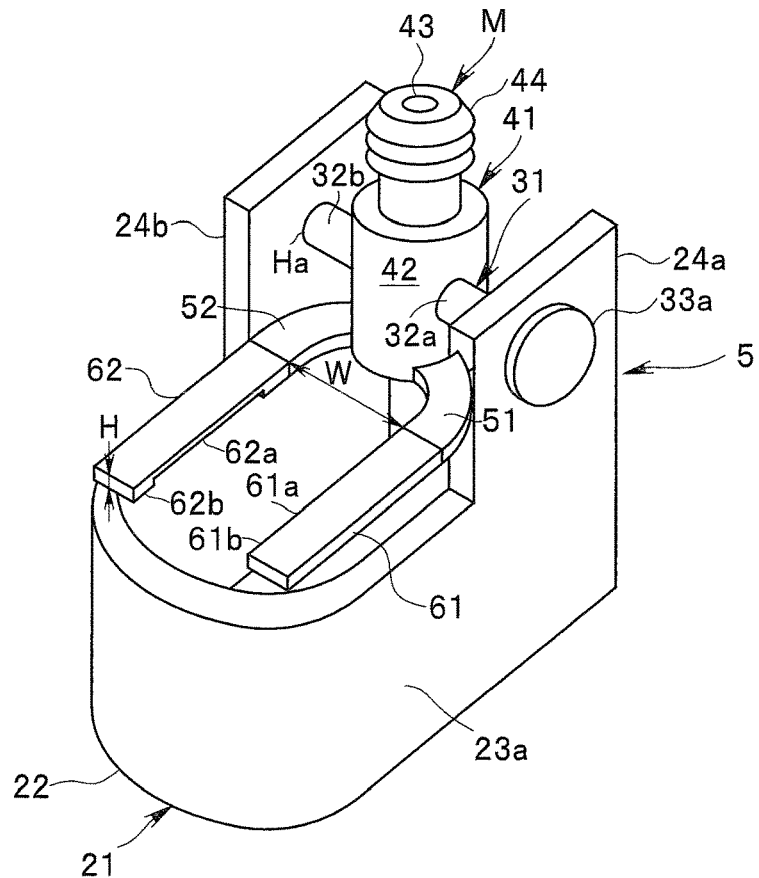
FIG. 5 is a perspective view showing an example of the endoscope connection portion of the endoscope leak test connector according to the first embodiment of the present invention.
Figure 6:
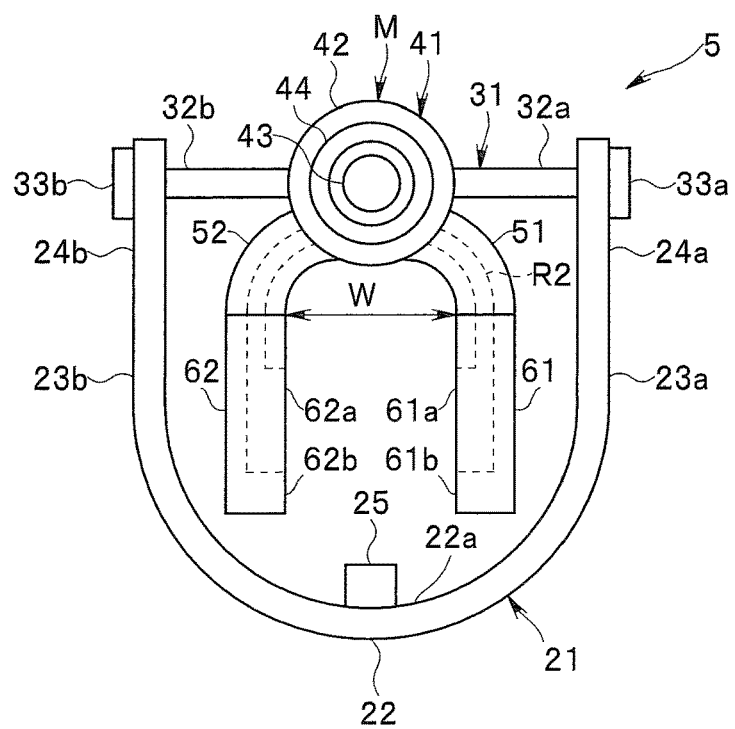
FIG. 6 is a plan view showing the example of the endoscope connection portion of the endoscope leak test connector according to the first embodiment of the present invention.
Figure 7:
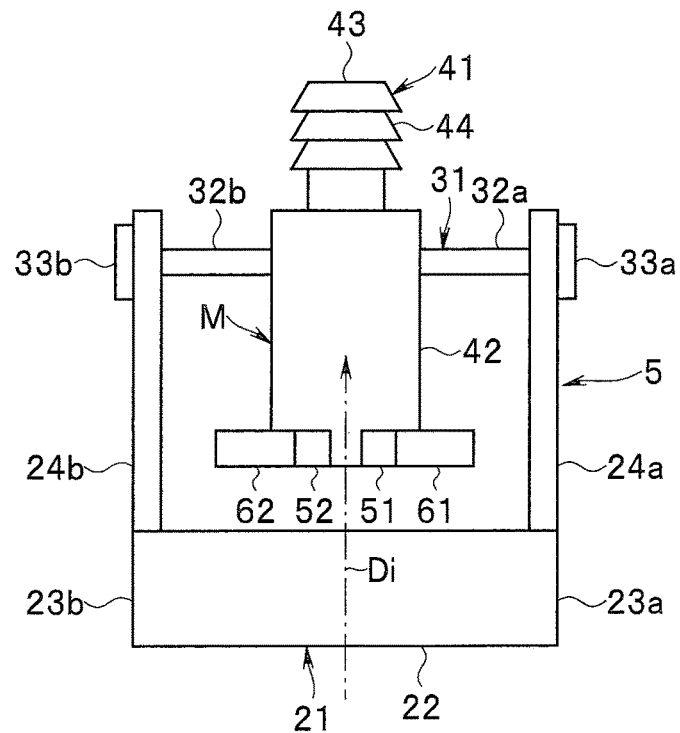
FIG. 7 is a front view showing the example of the endoscope connection portion of the endoscope leak test connector according to the first embodiment of the present invention.
Figure 8:
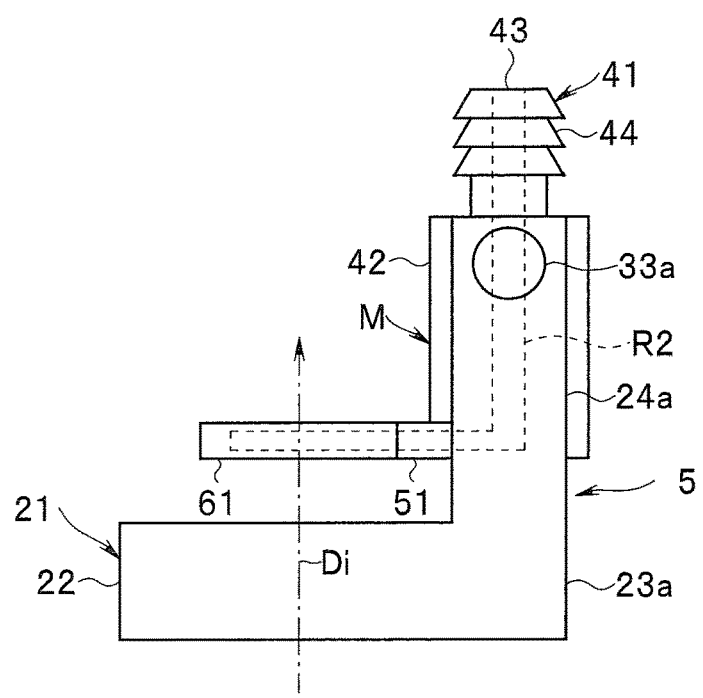
FIG. 8 is a side view showing the example of the endoscope connection portion of the endoscope leak test connector according to the first embodiment of the present invention.

FIGS. 5 to 8 are diagrams showing an example of the endoscope connection portion 5 of the endoscope leak test connector 3 according to the first embodiment of the present invention. FIG. 5 is a perspective view; FIG. 6 is a plan view; FIG. 7 is a front view; and FIG. 8 is a side view.

The endoscope connection portion 5 is configured to be capable of being connected with the leak test pipe sleeve 11. The endoscope connection portion 5 has a rotating body 21, a guiding member 31, a tube connection portion 41, branch portions 51 and 52, facing members 61 and 62, and a flow path R2.

Each of the rotating body 21, the guiding member 31, the tube connection portion 41 and the branch portion 51 is configured using metal, resin or the like as material. The rotating body 21 rotates the rotating ring 13 of the leak test pipe sleeve 11 to cause the leak test pipe sleeve 11 to be in either the valve opened state or the valve closed stated. The rotating body 21 has a center plate 22, side plates 23a and 23b, support plates 24a and 24b, and the connection-portion-side engagement portion 25.

The center plate 22, which is an operating member, is provided such that a width direction is in the insertion direction Di. The center plate 22 is provided being along a semicircular arc in a longitudinal direction so that one direction side forms a convex shape and the other direction side opposite to the one direction side forms a concave shape. A face of the center plate 22 on the other direction side constitutes a cover face 22a configured to non-liquid-tightly cover an outer circumferential portion of the leak test pipe sleeve 11. For example, the cover face 22a is provided being along a semicircular arc and having an inner diameter larger than an outer diameter of the leak test pipe sleeve 11 in a longitudinal direction, and non-liquid-tightly covers the outer circumferential portion of the leak test pipe sleeve 11.

Each of the side plates 23a and 23b is provided being extended in the other direction from both end portions of the center plate 22.

The support plates 24a and 24b are bent in an L shape at end portions of the side plates 23a and 23b, respectively, and are provided being extended in a direction corresponding to the insertion direction Di. The support plates 24a and 24b are provided with paired shaft holes Ha for attaching the guiding member 31, respectively, in a manner that the paired shaft holes Ha face each other.

The connection-portion-side engagement portion 25 is projectingly provided on the cover face 22a. The connection-portion-side engagement portion 25 is inserted inside the pipe-sleeve-side engagement portion 13a and is non-liquid-tightly engaged with the pipe-sleeve-side engagement portion 13a.

In other words, the rotating body 21 has the cover face 22a on an inner side, and the rotating body 21 causes the ventilation member 14 to project from the leak test pipe sleeve 11 by rotating in the positive direction and causes the ventilation member 14 to be buried into the leak test pipe sleeve 11 by rotating in the negative direction. The cover face 22a has the connection-portion-side engagement portion 25 configured to be non-liquid-tightly engaged with the pipe-sleeve-side engagement portion 13a of the leak test pipe sleeve 11 and non-liquid-tightly covers the outer circumferential portion of the leak test pipe sleeve 11.

The guiding member 31 rotatably supports the tube connection portion 41 and guides the facing members 61 and 62 to positions on planes intersecting the insertion direction Di of the rotating body 21. The guiding member 31 has rotation shafts 32a and 32b and engagement portions 33a and 33b.

The respective rotation shafts 32a and 32b are formed to have a diameter smaller than a diameter of the paired shaft holes Ha and are rotatably inserted through the paired shaft holes Ha. Each of the rotation shafts 32a and 32b rotatably supports the tube connection portion 41 relative to the rotating body 21.

The engagement portions 33a and 33b are provided on end portions of the rotation shafts 32a and 32b, respectively, and formed to have a diameter larger than the diameter of the paired shaft holes Ha. The engagement portions 33a and 33b engage with the rotation shafts 32a and 32b, respectively, so that the rotation shafts 32a and 32b do not fall off from the support plates 24a and 24b.

The tube connection portion 41 is configured so that the tube T can be connected. The tube connection portion 41 has a connection portion body 42, a gas inlet 43 and a slip-resisting projection 44.

The connection portion body 42 is formed in a tubular shape. The rotation shafts 32a and 32b are coupled with an outer circumferential portion of the connection portion body 42.

The gas inlet 43 is provided being extended in a distal end direction from the connection portion body 42. The tube T is externally fitted to the gas inlet 43. In other words, the gas inlet 43 is connected with the endoscope reprocessor 1 which is a gas supply source.

The slip-resisting projection 44 is provided on an outer circumferential portion of the gas inlet 43. The slip-resisting projection 44 increases frictional force against the tube T to prevent the tube T from falling off.

The branch portions 51 and 52 branch in two directions from a proximal end portion of the connection portion body 42. The branch portions 51 and 52 are formed such that end portions on one direction side are separated from each other by the predetermined width W.

The facing members 61 and 62 are configured using rubber or the like as material. The facing members 61 and 62 are attached to the end portions of the branch portions 51 and 52 on the one direction side, respectively. The facing members 61 and 62 have the same thickness as the predetermined height H so that the facing members 61 and 62 can be fitted to the neck portion 14b in a state of being liquid-tight from the outside and are arranged in parallel being separated from each other by the predetermined width W. The facing members 61 and 62 face the ventilation member 14 which is in a state of projecting from the leak test pipe sleeve 11. The facing members 61 and 62 have gas outlets 61a and 62a, and seal portions 61b and 62b.

The gas outlets 61a and 62a are provided at positions facing the ventilation member opening 14d. The gas outlets 61a and 62a communicate with the gas inlet 43 and are open on the facing members 61 and 62.

The seal portions 61b and 62b are provided on circumferential edges of the gas outlets 61a and 62a. The seal portions 61b and 62b are arranged on the facing members 61 and 62 and seal the gas outlets 61a and 62a and the ventilation member 14 so that the gas outlets 61a and 62a liquid-tightly communicate with the ventilation member 14.

The flow path R2 is provided inside the tube connection portion 41, the branch portions 51 and 52 and the facing members 61 and 62.

In other words, the tube connection portion 41, the branch portions 51 and 52 and the facing members 61 and 62 constitute a moving body M that moves relative to the rotating body 21.

The guiding member 31 is arranged in the rotating body 21 and has the rotation shafts 32a and 32b configured to rotatably support the moving body M.

The branch portions 51 and 52 and the facing members 61 and 62 form a recess portion of the moving body M. The guiding member 31 causes the moving body M to move to guide the facing members 61 and 62 so that the facing members 61 and 62 face the ventilation member 14 that has entered the recess portion.

(Operation)

An operation of the endoscope connection portion 5 of the endoscope leak test connector 3 will be described.

Figure 9:
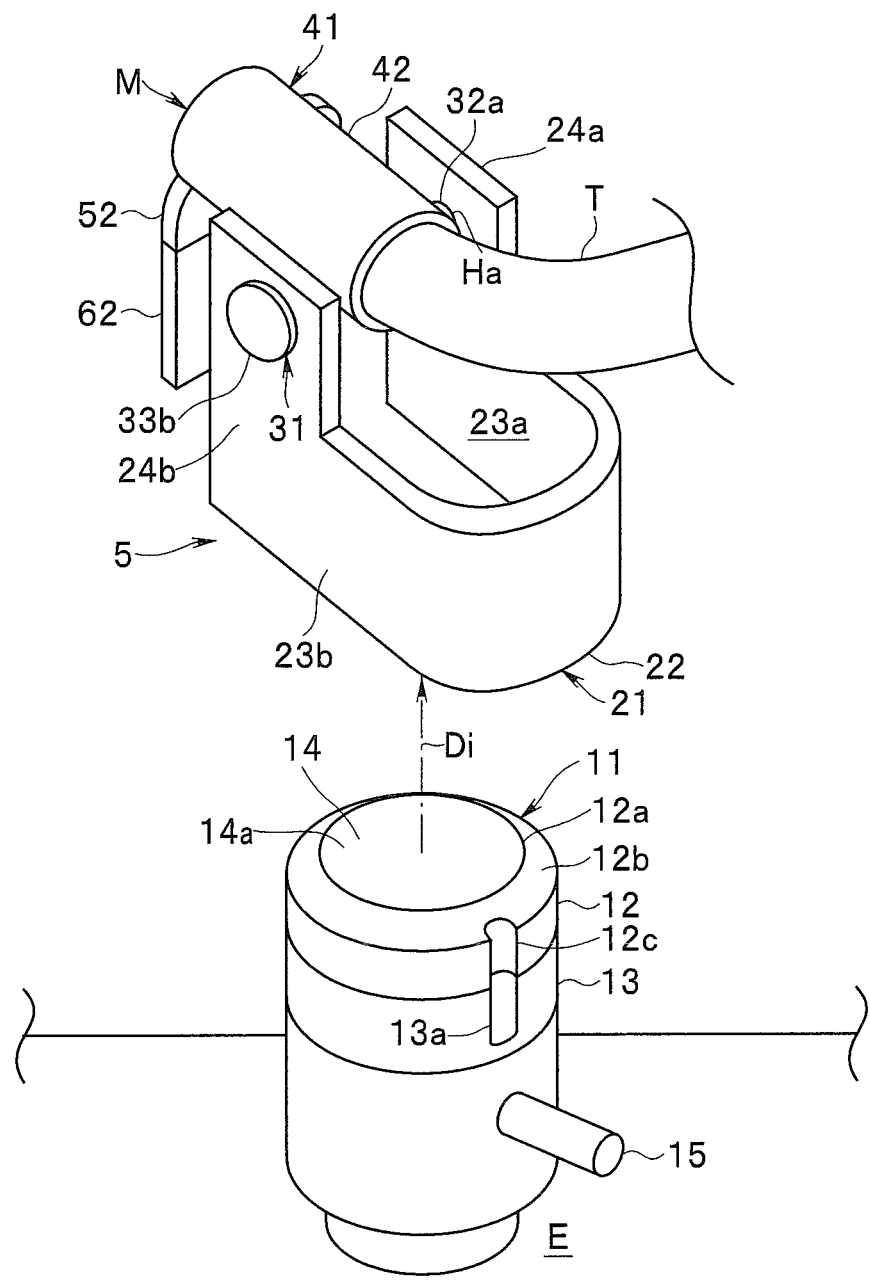
FIG. 9 is an explanatory diagram for illustrating an example of connection between the endoscope connection portion of the endoscope leak test connector and the leak test pipe sleeve according to the first embodiment of the present invention.
Figure 10:
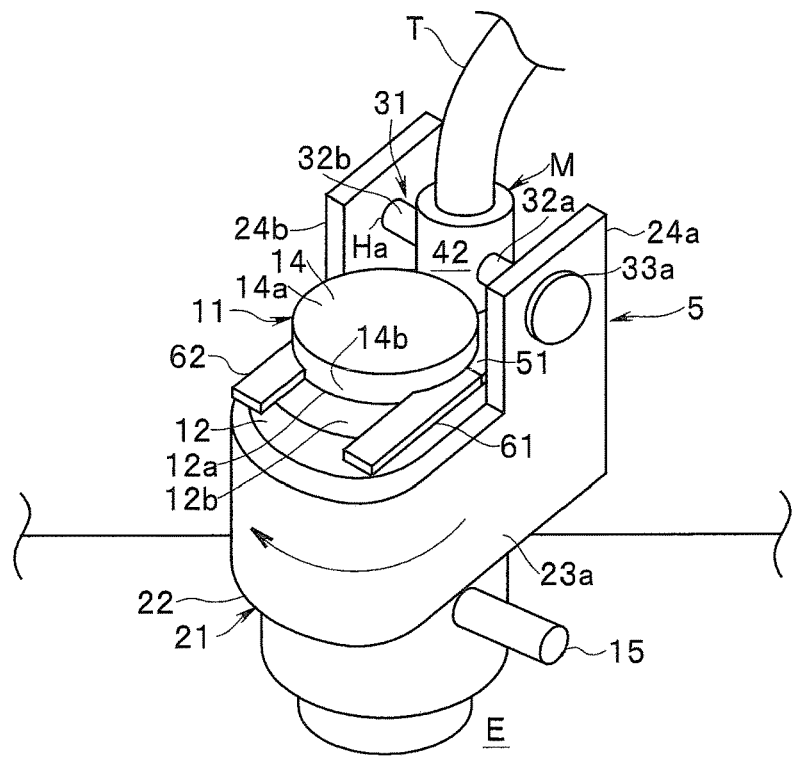
FIG. 10 is an explanatory diagram for illustrating the example of connection between the endoscope connection portion of the endoscope leak test connector and the leak test pipe sleeve according to the first embodiment of the present invention.

FIGS. 9 and 10 are explanatory diagrams for illustrating an example of connection between the endoscope connection portion 5 of the endoscope leak test connector 3 and the leak test pipe sleeve 11 according to the first embodiment of the present invention.

As shown in FIG. 9, the tube T is attached to the tube connection portion 41 beforehand. The ventilation member 14 is buried in the trunk portion 12. In order that insertion of the leak test pipe sleeve 11 is not disturbed, a user causes the tube connection portion 41 to rotate around the guiding member 31 to cause the facing members 61 and 62 to move outward from a predetermined position where the leak test pipe sleeve 11 is to be arranged. Then, by inserting the leak test pipe sleeve 11 into the rotating body 21 in the insertion direction Di and inserting the connection-portion-side engagement portion 25 into the pipe-sleeve-side engagement portion 13a, the user arranges the leak test pipe sleeve 11 at the predetermined position.

As shown in FIG. 10, when the user causes the rotating body 21 to rotate in the positive direction, the pipe-sleeve-side engagement portion 13a and the rotating ring 13 rotate. The pair of parallel side faces 14b1 of the ventilation member 14 projects from the trunk portion 12 in a direction corresponding to a fitting direction of the facing members 61 and 62. The ventilation member opening 14d provided inside the leak test pipe sleeve 11 is exposed outside. The leak test pipe sleeve 11 enters the valve opened state.

Figure 11:
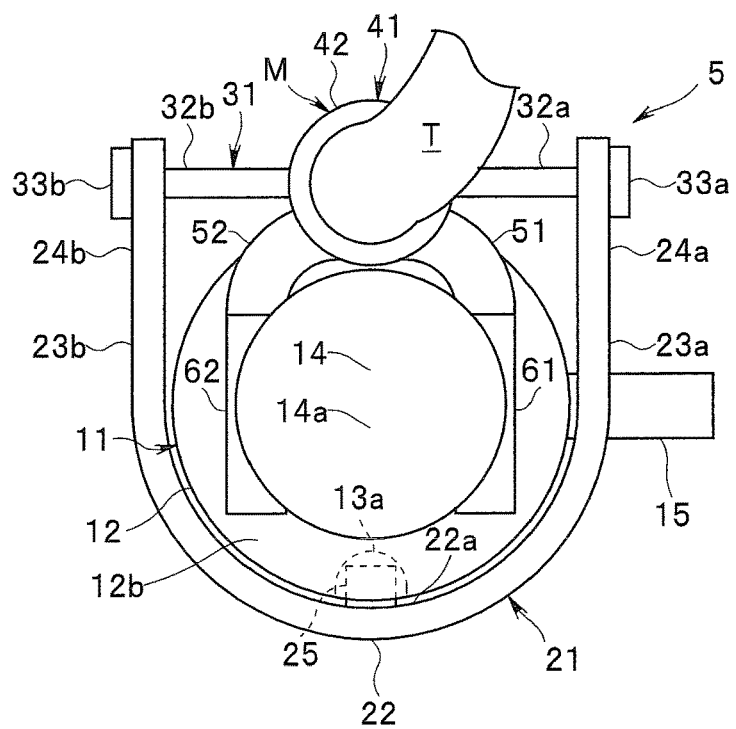
FIG. 11 is a plan view showing the example of connection between the endoscope connection portion of the endoscope leak test connector and the leak test pipe sleeve according to the first embodiment of the present invention.

As shown in FIG. 11, when the user causes the tube connection portion 41 to rotate around the guiding member 31 and fits the facing members 61 and 62 to the neck portion 14b in the fitting direction, the gas outlets 61a and 62a liquid-tightly communicate with the ventilation member opening 14d by the seal portions 61b and 62b.

Figure 12:
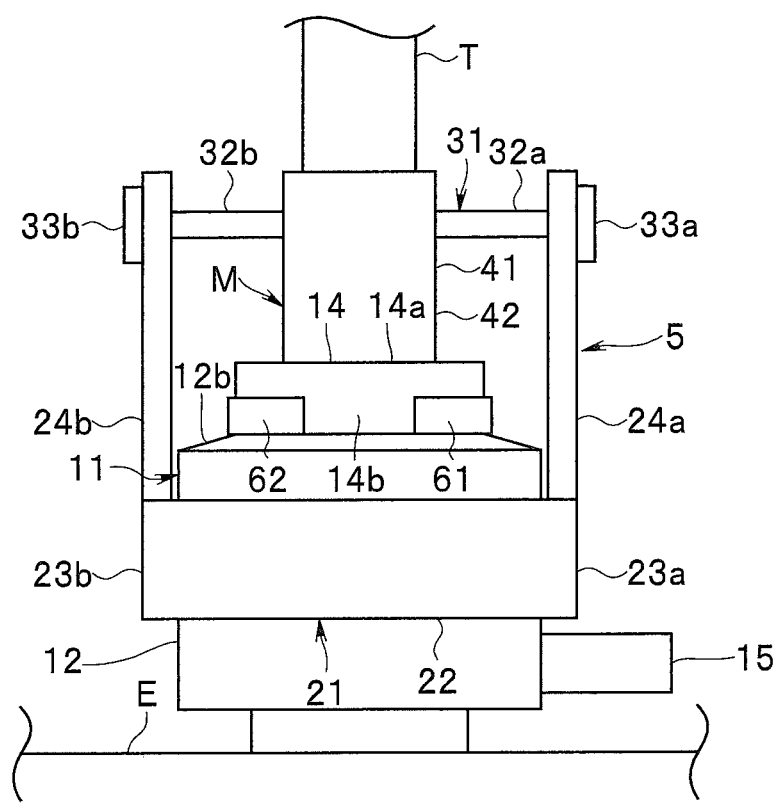
FIG. 12 is a front view showing the example of connection between the endoscope connection portion of the endoscope leak test connector and the leak test pipe sleeve according to the first embodiment of the present invention.
Figure 13:
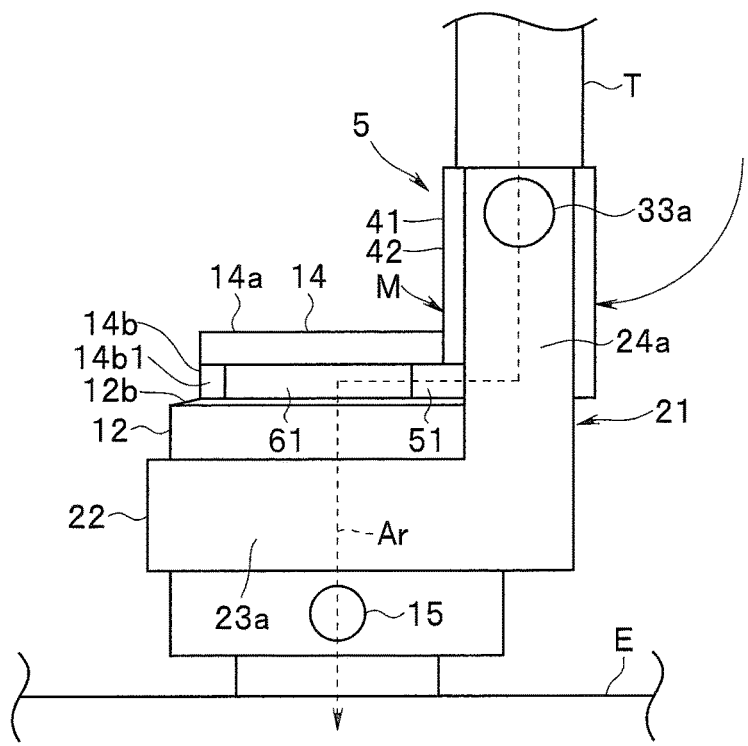
FIG. 13 is a side view showing the example of connection between the endoscope connection portion of the endoscope leak test connector and the leak test pipe sleeve according to the first embodiment of the present invention.

As shown in FIGS. 12 and 13, when the gas outlets 61a and 62a communicate with the ventilation member opening 14d, the flow paths R1, R1a and R2 communicate with one another. The endoscope connection portion 5 and the leak test pipe sleeve 11 are connected with each other.

The user may further connect the endoscope reprocessor 1 and the endoscope E by an endoscope connection tube for reprocessing not shown.

When the endoscope E is caused to be immersed in liquid, the outer circumferential portion of the trunk portion 12, the distal end circumferential edge 12b, an outer circumferential portion of the rotating ring 13 and a distal end face of the lid portion 14a, which constitute an outer surface of the leak test pipe sleeve 11, come into contact with liquid.

The endoscope reprocessor 1 feeds gas Ar into the endoscope E and performs a leak test.

After the leak test ends, by removing the facing members 61 and 62 from the neck portion 14b by causing the tube connection portion 41 to rotate around the guiding member 31 and causing the ventilation member 14 to be buried into the trunk portion 12 by rotating the rotating body 21 in the negative direction, the user causes the leak test pipe sleeve 11 to enter the valve closed state.

According to the first embodiment, the endoscope leak test connector 3 can be connected with the leak test pipe sleeve 11 so that a whole outer surface of the leak test pipe sleeve 11 which may be contaminated can come into contact with external liquid.

Modification of First Embodiment

Though the facing members 61 and 62 are fitted to the leak test pipe sleeve 11 by rotation of the moving body M in the first embodiment, a configuration may be made in which the facing members 61 and 62 are fitted to the leak test pipe sleeve 11 by sliding of the moving body M.

Figure 14:
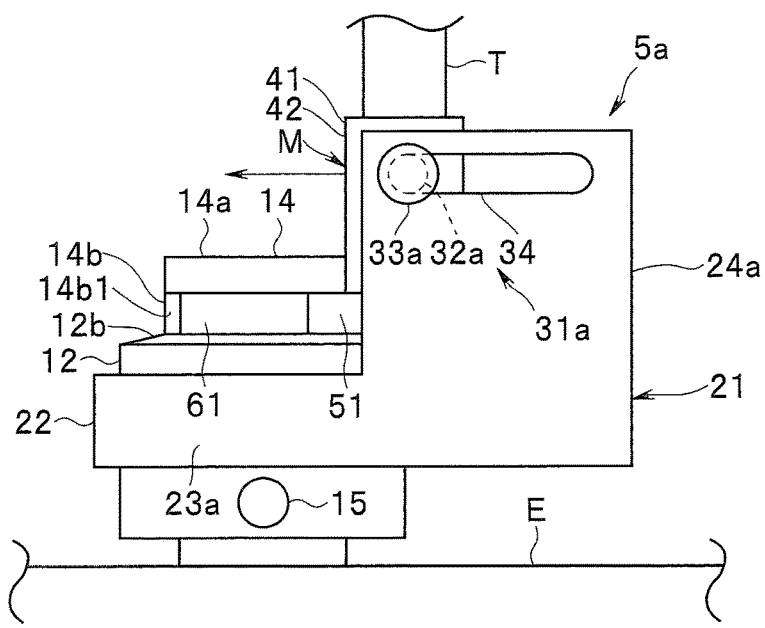
FIG. 14 is a side view showing an example of an endoscope connection portion of an endoscope leak test connector according to a modification of the first embodiment of the present invention.

FIG. 14 is a side view showing an example of an endoscope connection portion 5a of the endoscope leak test connector 3 according to a modification of the first embodiment of the present invention. In the present modification, description of examples of the same components as the first embodiment will be omitted.

A guiding member 31a has slide holes 34 constituting tracks through which the moving body M slides.

The slide holes 34 are provided in the support plates 24a and 24b, respectively, and are formed extending in width directions of the support plates 24a and 24b. A hole width of the slide holes 34 is set larger than a width of the rotation shafts 32a and 32b and smaller than a width of the engagement portions 33a and 33b.

In order that insertion of the leak test pipe sleeve 11 is not disturbed, the user causes the tube connection portion 41 to slide in the other direction along the slide holes 34 to cause the facing members 61 and 62 to move outward from predetermined positions. The user inserts the leak test pipe sleeve 11 into the rotating body 21 and arranges the leak test pipe sleeve 11 at a predetermined position, and inserts the connection-portion-side engagement portion 25 into the pipe-sleeve-side engagement portion 13a.

When the user causes the rotating body 21 to rotate in the positive direction, the ventilation member opening 14d is exposed outside. The leak test pipe sleeve 11 enters the valve opened state.

When the user causes the tube connection portion 41 to slide in one direction along the slide holes 34, the facing members 61 and 62 are fitted to the neck portion 14b, and the endoscope connection portion 5a and the leak test pipe sleeve 11 are connected with each other.

When the user causes the tube connection portion 41 to slide in the other direction after a leak test ends, the facing members 61 and 62 are removed from the neck portion 14b.

In other words, the guiding member 31a is arranged in the rotating body 21 and has tracks configured to slidably support the moving body M.

According to the modification of the first embodiment, the endoscope leak test connector 3, can attach or detach the facing members 61 and 62 by sliding the moving body M so as to prevent elastic deformation, and can connect with the leak test pipe sleeve 11 so that the whole outer surface of the leak test pipe sleeve 11 which may be contaminated can come in contact with external liquid.

Second Embodiment

Though the facing members 61 and 62 are arranged at positions on planes intersecting the insertion direction Di in the first embodiment and the modification, the facing members 61 and 62 may be provided on an inner circumferential portion of a tube body 71 in the insertion direction Di.

Figure 15:
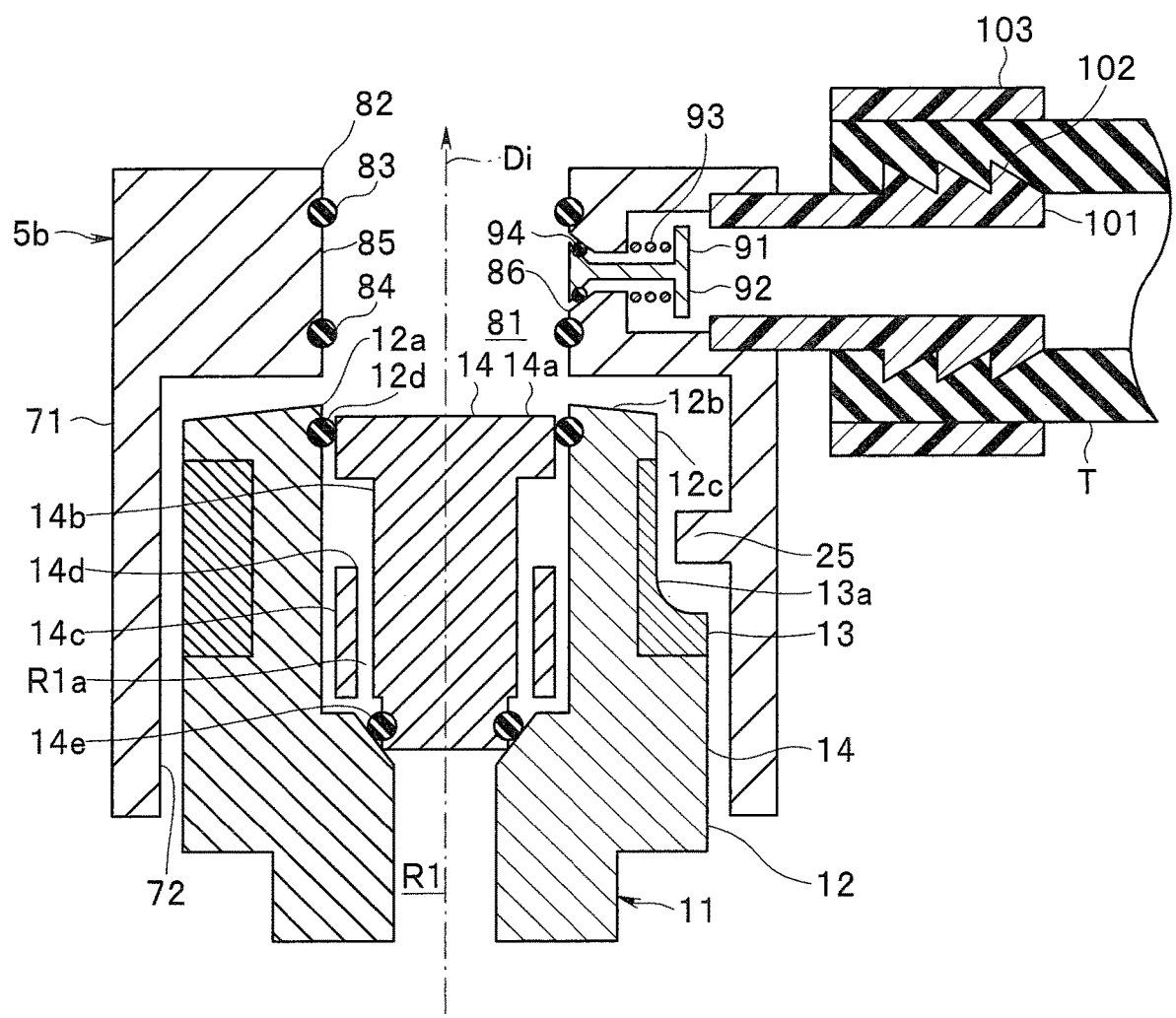
FIG. 15 is a cross-sectional view showing an example of an endoscope connection portion of an endoscope leak test connector according to a second embodiment of the present invention.
Figure 16:
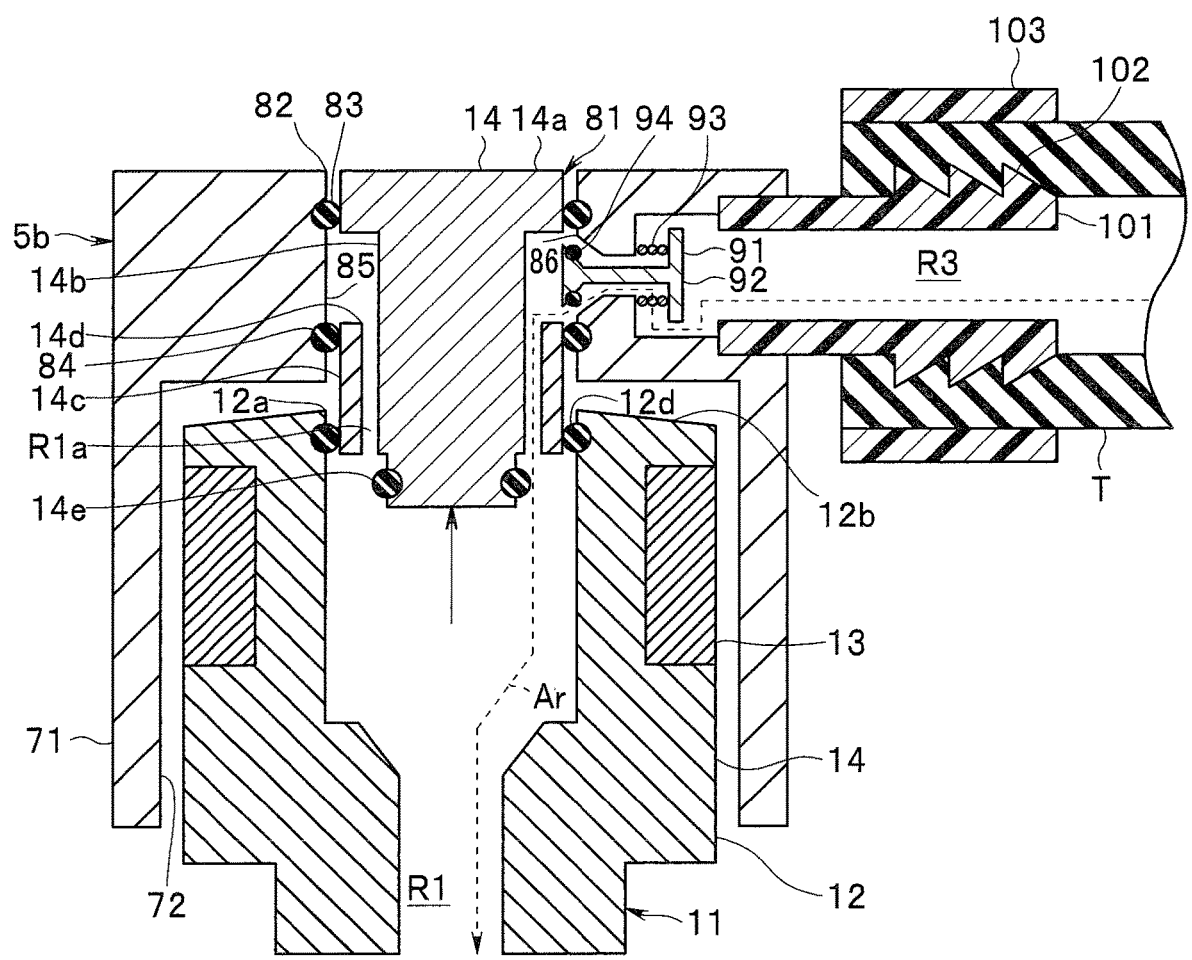
FIG. 16 is a cross-sectional view showing the example of the endoscope connection portion of the endoscope leak test connector according to the second embodiment of the present invention.

FIGS. 15 and 16 are cross-sectional diagrams showing an example of an endoscope connection portion 5b of the endoscope leak test connector 3 according to a second embodiment of the present invention. FIGS. 15 and 16 show sections of the endoscope connection portion 5b. In the present embodiment, description of examples of the same components as the first embodiment and the modification of the first embodiment will be omitted.

The endoscope connection portion 5b has the tube body 71, a ventilation member accommodating portion 81, a flow path R3, a check valve 91 and a gas inlet 101.

The tube body 71 is configured, for example, using metal, or resin as material. The tube body 71 is formed in a tubular shape so as to be fitted onto the leak test pipe sleeve 11. The tube body 71 has a cover face 72 formed to non-liquid-tightly cover the outer circumferential portion of the leak test pipe sleeve 11 on an inner side. For example, the cover face 72 is provided being along an arc and having an inner diameter larger than the outer diameter of the leak test pipe sleeve 11, and non-liquid-tightly covers the outer circumferential portion of the leak test pipe sleeve 11. On the cover face 72, the connection-portion-side engagement portion 25 to be inserted into the pipe-sleeve-side engagement portion 13a is projectingly provided.

The ventilation member accommodating portion 81 is provided on a distal end portion of the tube body 71. The ventilation member accommodating portion 81 has an inner diameter smaller than the outer diameter of the leak test pipe sleeve 11, and the ventilation member 14 projecting from the trunk portion 12 is accommodated in the ventilation member accommodating portion 81. The distal end face of the lid portion 14a is exposed outside via a distal-end-side opening 82 of the ventilation member accommodating portion 81. The ventilation member accommodating portion 81 has seal portions 83 and 84.

The seal portion 83 is configured with an O-shaped ring using rubber or the like as material. The seal portion 83 is provided on an inner circumferential wall of the ventilation member accommodating portion 81 on a distal end side and makes the neck portion 14b and the ventilation member opening 14d liquid-tight from outside by hitting the outer circumferential portion of the lid portion 14a projecting from the trunk portion 12.

The seal portion 84 is configured with an O-shaped ring using rubber or the like as material. The seal portion 84 is provided on the inner circumferential wall of the ventilation member accommodating portion 81 on a proximal end side, and makes the neck portion 14b and the ventilation member opening 14d liquid-tight from outside by hitting the outer circumferential portion of the ventilation member body 14c. An inner circumferential portion of the ventilation member accommodating portion 81 between the seal portions 83 and 84 constitutes a facing member 85. On the facing member 85, a gas outlet 86 communicating with the gas inlet 101 is open.

In other words, the seal portions 83 and 84 are 0-shaped rings provided on the distal end side and the proximal end side of the inner circumferential wall of the ventilation member accommodating portion 81.

The check valve 91 is provided at the gas outlet 86. The check valve 91 causes the gas Ar to flow in a forward direction toward the ventilation member accommodating portion 81 from the gas inlet 101 and prevents the gas Ar from flowing in a backward direction. The check valve 91 has a valve stem 92, a coil spring 93 and an O-shaped ring 94.

The valve stem 92 is configured using metal, resin or the like as material. The valve stem 92 has a stopper on one end portion and a spring holder on the other end portion and is inserted in the gas outlet 86. A diameter of the stopper conically increases toward one end portion, and the O-shaped ring 94 is provided on a conical surface and is stopped at a circumferential edge of the gas outlet 86 on the ventilation member accommodating portion 81 side.

The coil spring 93 is configured with metal or the like and is provided surrounding an outer circumferential portion of the valve stem 92. By one end pressing against a circumferential edge of the gas outlet 86 on the gas inlet 101 side and the other end pressing against the spring holder, the valve stem 92 is urged in a direction to blockade the gas outlet 86.

The gas inlet 101 is attached to an outer circumferential portion of the ventilation member accommodating portion 81 to communicate with the gas outlet 86. For the gas inlet 101, the tube T is fitted onto a slip-resisting projection 102, and a fall preventing ring 103 is attached outside the tube T.

In other words, the cover face 72 and the facing member 85 are arranged on the inner circumferential portion of the tube body 71.

As shown in FIG. 16, the user fits the tube body 71 over the leak test pipe sleeve 11 and covers the outer circumferential portion of the trunk portion 12 with the cover face 72. The user inserts the connection-portion-side engagement portion 25 into the pipe-sleeve-side engagement portion 13*a*. When the user causes the tube body 71 to rotate in the positive direction, the pipe-sleeve-side engagement portion 13*a* and the rotating ring 13 rotate by the connection-portion-side engagement portion 25. The ventilation member 14 projects from the trunk portion 12, is accommodated into the ventilation member accommodating portion 81, and faces the facing member 85. The ventilation member opening 14*d* and the gas outlet 86 liquid-tightly communicate with each other by the seal portions 83 and 84. The leak test pipe sleeve 11 enters the valve opened state.

When the endoscope E is caused to be immersed in liquid, the outer circumferential portion of the trunk portion 12, the distal end circumferential edge 12*b*, the outer circumferential portion of the rotating ring 13 and the distal end face of the lid portion 14*a*, which constitute the outer surface of the leak test pipe sleeve 11, come into contact with liquid.

The endoscope reprocessor 1 introduces the gas Ar from the gas inlet 101. When the gas Ar is introduced, the check valve 91 opens, and the gas Ar is introduced into the leak test pipe sleeve 11 via the gas outlet 86 and the ventilation member opening 14*d*.

When the user causes the tube body 71 to rotate in the negative direction after a leak test ends, the ventilation member 14 is buried into the trunk portion 12.

According to the second embodiment, the endoscope leak test connector 3 can enhance sealability with the ventilation member 14, and can connect with the leak test pipe sleeve 11 so that the whole outer surface of the leak test pipe sleeve 11 which may be contaminated can come into contact with external liquid.

Furthermore, according to the second embodiment, the endoscope leak test connector 3 can, by fitting the tube body 71 onto the leak test pipe sleeve 11 and causing the tube body 71 to rotate in the positive direction, cause the ventilation member opening 14*d* and the gas outlet 86 to communicate with each other. Therefore, in the second embodiment, the endoscope leak test connector 3 does not require a troublesome work of connecting the moving body M by the user, and it does not happen that attachment of the moving body M is forgotten or that the moving body M comes off.

Modification of Second Embodiment

Though the seal portions 83 and 84 are configured with the O-shaped rings provided on the inner circumferential wall of the ventilation member accommodating portion 81 in the second embodiment, a seal portion 87 may be configured with an inner circumferential wall of a ventilation member accommodating portion 81*a*.

Figure 17:
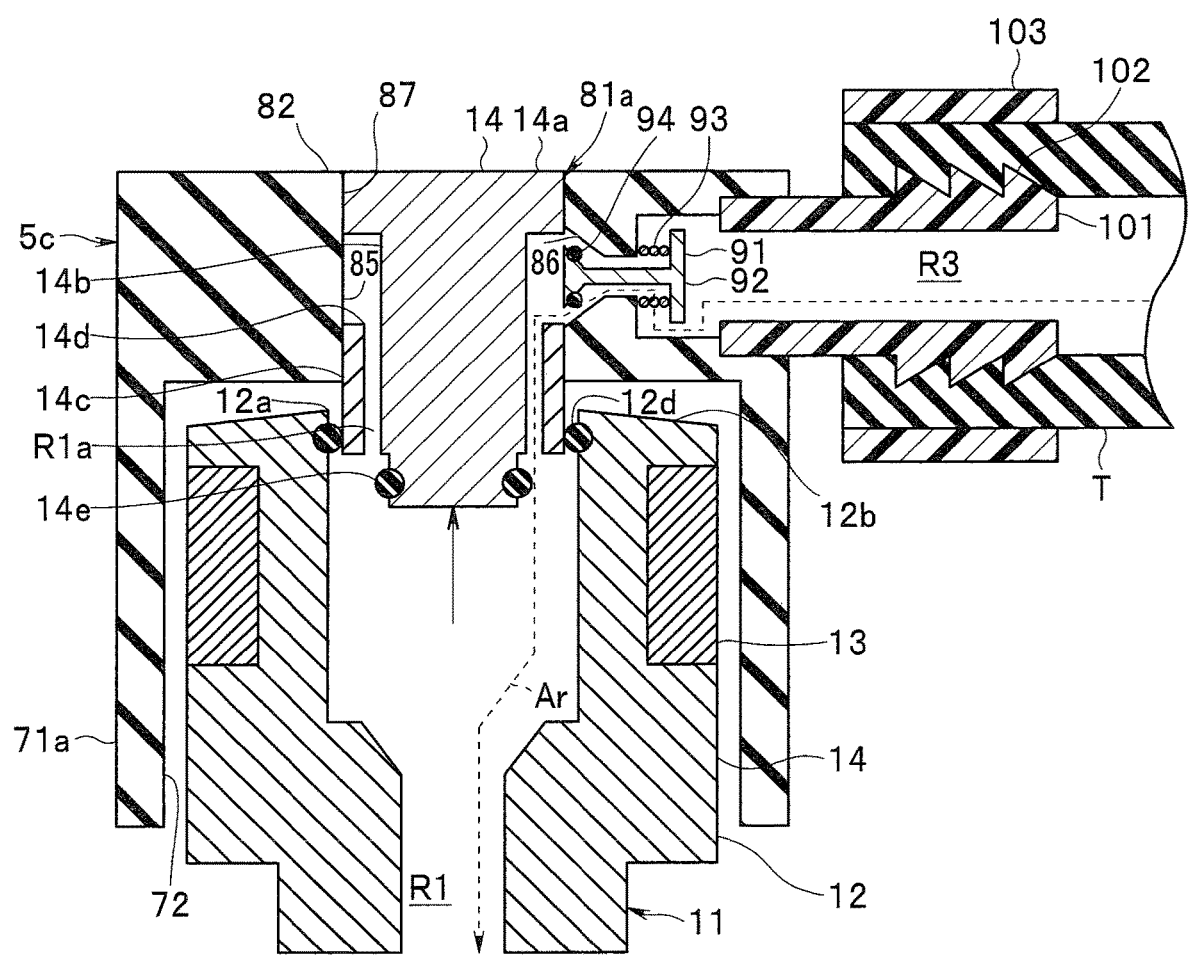
FIG. 17 is a cross-sectional view showing an example of an endoscope connection portion of an endoscope leak test connector according to a modification of the second embodiment of the present invention.

FIG. 17 is a cross-sectional view showing an example of an endoscope connection portion 5*c* of the endoscope leak test connector 3 according to a modification of the second embodiment of the present invention. FIG. 17 shows a section of the endoscope connection portion 5*c*. In the present modification, description of examples of the same components as the first and second embodiments and the modification of the first embodiment will be omitted.

Inner circumferential walls of a tube body 71*a* and the ventilation member accommodating portion 81*a* are configured using elastically deformable rubber or the like as material. An inner diameter of the ventilation member accommodating portion 81*a* is set equal to or smaller than an outer diameter of the ventilation member 14 so that the ventilation member 14 is liquid-tightly accommodated. When the inner diameter of the ventilation member accommodating portion 81*a* is set smaller than the outer diameter of the ventilation member 14, the inner diameter of the ventilation member accommodating portion 81*a* is increased by elastic deformation, and the ventilation member 14 is accommodated. An inner circumferential wall of the ventilation member accommodating portion 81*a* constitutes the seal portion 87.

When the ventilation member 14 is accommodated, the lid portion 14*a* and the ventilation member body 14*c* presses against the seal portion 87. The seal portion 87 causes the gas outlet 86 and the ventilation member 14 to liquid-tightly communicate with each other.

In other words, the seal portion 87 is the inner circumferential wall of the ventilation member accommodating portion 81*a*.

According to the modification of the second embodiment, the seal portion 87 can be configured with the inner circumferential wall of the ventilation member accommodating portion 81*a*, and can connect with the leak test pipe sleeve 11 so that the whole outer surface of the leak test pipe sleeve 11 which may be contaminated can come into contact with external liquid.

Note that though the pipe-sleeve-side engagement portion 13*a* is formed in a recess portion, and the connection-portion-side engagement portion 25 is formed in a projecting shape in the embodiments and the modifications, the pipe-sleeve-side engagement portion 13*a* may be formed in a projecting shape, and the connection-portion-side engagement portion 25 may be formed in a recess shape.

Note that though the endoscope connection portions 5*b* and 5*c* have the check valve 91 in the second embodiment and the modification of the second embodiment, the endoscope connection portion 5*b* and 5*c* may not have the check valve 91.

The present invention is not limited to the embodiments described above, and various changes, alterations and the like are possible within a range not changing the spirit of the present invention.

According to the present invention, an endoscope leak test connector can be provided that can be connected with a leak test pipe sleeve so that a whole outer surface of the leak test pipe sleeve which may be contaminated can come into contact with external liquid.

What is claimed is:

1. An endoscope leak test connector comprising:
   a cover face including a connection portion-side engagement portion configured to be non-liquid-tightly engaged with a pipe-sleeve-side engagement portion of a leak test pipe sleeve for an endoscope, the leak test pipe sleeve comprising a rotating ring, the pipe-sleeve-side engagement portion being provided on the rotating ring, and a ventilation member configured to project and be buried in conjunction with a rotation operation of the rotating ring, the cover face non-liquid-tightly covering an outer circumferential portion of the leak test pipe sleeve;

a rotating body comprising the cover face on an inner side and configured to cause the ventilation member to project from the leak test pipe sleeve by rotating in a positive direction and cause the ventilation member to be buried into the leak test pipe sleeve by rotating in a negative direction;

a gas inlet configured to be connected with a gas supply source;

a facing member configured to face the ventilation member that is in a state of projecting from the leak test pipe sleeve;

a gas outlet communicating with the gas inlet and being open on the facing member; and a seal portion arranged on the facing member and configured to seal the gas outlet and the ventilation member so that the gas outlet and the ventilation member liquid-tightly communicate with each other.

2. The endoscope leak test connector according to claim 1, comprising:

a moving body, in which the facing member forms a recess portion of the moving body; and a guiding member configured to cause the moving body to move to guide the facing member so that the facing member faces the ventilation member moved into the recess portion.

3. The endoscope leak test connector according to claim 2, wherein the guiding member is arranged on the moving body and includes a rotation shaft rotatably supporting the moving body.

4. The endoscope leak test connector according to claim 2, wherein the guiding member is arranged on the moving body and includes a track slidably supporting the moving body.

5. The endoscope leak test connector according to claim 1, comprising a tube body; wherein the cover face and the facing member are arranged on an inner circumferential portion of the tube body.

6. The endoscope leak test connector according to claim 5, wherein the tube body includes a ventilation member accommodating portion configured to accommodate the ventilation member; and the seal portion is an O-shaped ring provided on a distal end side and a proximal end side of an inner circumferential wall of the ventilation member accommodating portion.

7. The endoscope leak test connector according to claim 5, wherein the tube body includes a ventilation member accommodating portion configured to accommodate the ventilation member; and the seal portion is the inner circumferential wall of the ventilation member accommodating portion.

8. An endoscope leak tester comprising:

the endoscope leak test connector according to claim 1; and a gas supply source configured to be connected with the gas inlet.

9. An endoscope reprocessor comprising:

the endoscope leak test connector according to claim 1;

a treatment tank configured so that the endoscope is arranged;

a gas supply source; and a reprocessor connection portion arranged in the treatment tank, communicating with the gas supply source and configured to be connected with the gas inlet.

10. An endoscope leak test connector comprising:

a cover face including a connection portion-side engagement portion configured to be non-liquid-tightly engaged with a pipe-sleeve-side engagement portion of a leak test pipe sleeve for an endoscope, the leak test pipe sleeve comprising the pipe-sleeve-side engagement portion and a ventilation member capable of projecting and being buried, the cover face non-liquid-tightly covering an outer circumferential portion of the leak test pipe sleeve;

an operating member comprising the cover face on an inner side and configured to cause the ventilation member to be buried into the leak test pipe sleeve by causing the ventilation member to project from the leak test pipe sleeve;

a gas inlet configured to be connected with a gas supply source;

a facing member configured to face the ventilation member that is in a state of projecting from the leak test pipe sleeve;

a gas outlet communicating with the gas inlet and being open on the facing member; and a seal portion arranged on the facing member and configured to seal the gas outlet and the ventilation member so that the gas outlet and the ventilation member liquid-tightly communicate with each other.

* * * * *